US006759619B2

(12) United States Patent
Nieto

(10) Patent No.: US 6,759,619 B2
(45) Date of Patent: Jul. 6, 2004

(54) SURGICAL SCALPEL ELECTRICAL INCINERATING DEVICE

(76) Inventor: Javier Ortega Nieto, Tezoquipa 40 Col., Tlalpan C.P. 14000 D.F. (MX)

(*) Notice: Subject to any disclaimer, the term of this patent is extended or adjusted under 35 U.S.C. 154(b) by 0 days.

(21) Appl. No.: 10/296,271

(22) PCT Filed: Mar. 1, 2001

(86) PCT No.: PCT/MX01/00015
§ 371 (c)(1),
(2), (4) Date: Nov. 22, 2002

(87) PCT Pub. No.: WO01/95961
PCT Pub. Date: Dec. 20, 2001

(65) Prior Publication Data
US 2003/0160027 A1 Aug. 28, 2003

(30) Foreign Application Priority Data
Jun. 16, 2000 (MX) .............................. 005877

(51) Int. Cl.[7] .................... B23K 11/22; A61L 11/00; A61G 12/00
(52) U.S. Cl. ...................................... 219/68
(58) Field of Search .................... 219/68; 110/250, 110/346

(56) References Cited

U.S. PATENT DOCUMENTS 5,138,125 A    8/1992  Salesses
5,545,869 A    8/1996  Piva
5,736,706 A  * 4/1998  Butler ........................ 219/68
6,337,454 B1 * 1/2002  Walker ....................... 219/68
6,621,031 B2 * 9/2003  Stevens ..................... 219/69.1

FOREIGN PATENT DOCUMENTS

| EP | 913163 A2 | * | 5/1999 |
| ES | 273776 U | | 7/1984 |
| ES | 1002776 U | | 6/1988 |
| FR | 2719991 | | 11/1995 |
| FR | 2766375 A1 | * | 1/1999 |
| JP | 1-285268 A | * | 11/1989 |
| WO | WO9528972 | | 11/1995 |

* cited by examiner

Primary Examiner—Geoffrey S. Evans
(74) Attorney, Agent, or Firm—Kleinberg & Lerner, LLP; Finn T. Simmensen

(57) ABSTRACT

A surgical scalpel incinerator an electromechanism for thermally destroying and sterilizing scalpels: a cabinet having a door through which a scalpel blade is inserted and supported by supports above several metal plates. Closing the door withdraws the supports, after which the blade contacts the plates. Closing the door closes a switch, connecting the plates to a power supply, electrifying the blade. Pressure plates on the door urge the blade against the plates. Sterilized scrap of the blade falls between the plates and into a receptacle in a drawer beneath the plates.

13 Claims, 6 Drawing Sheets

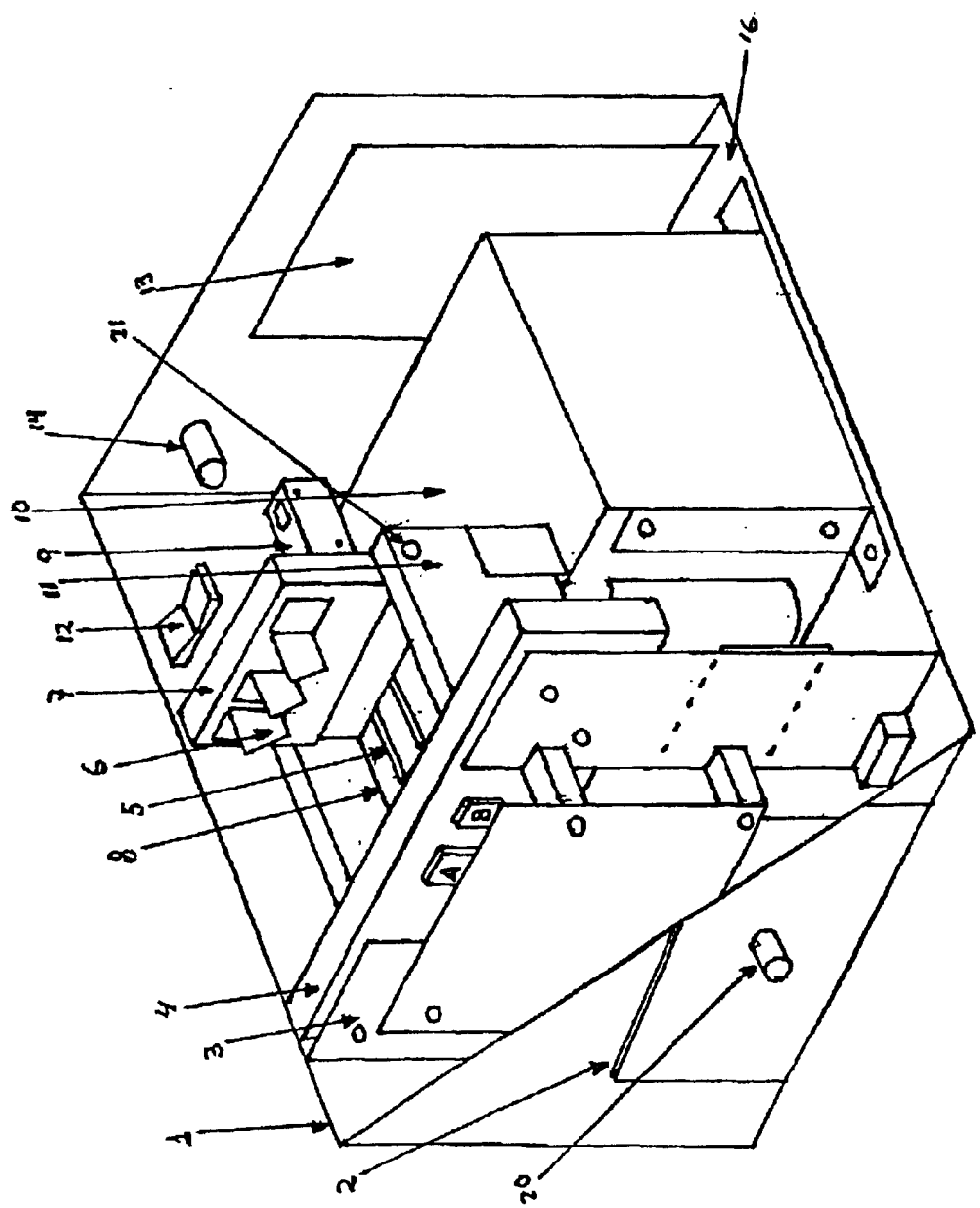
Figura 1

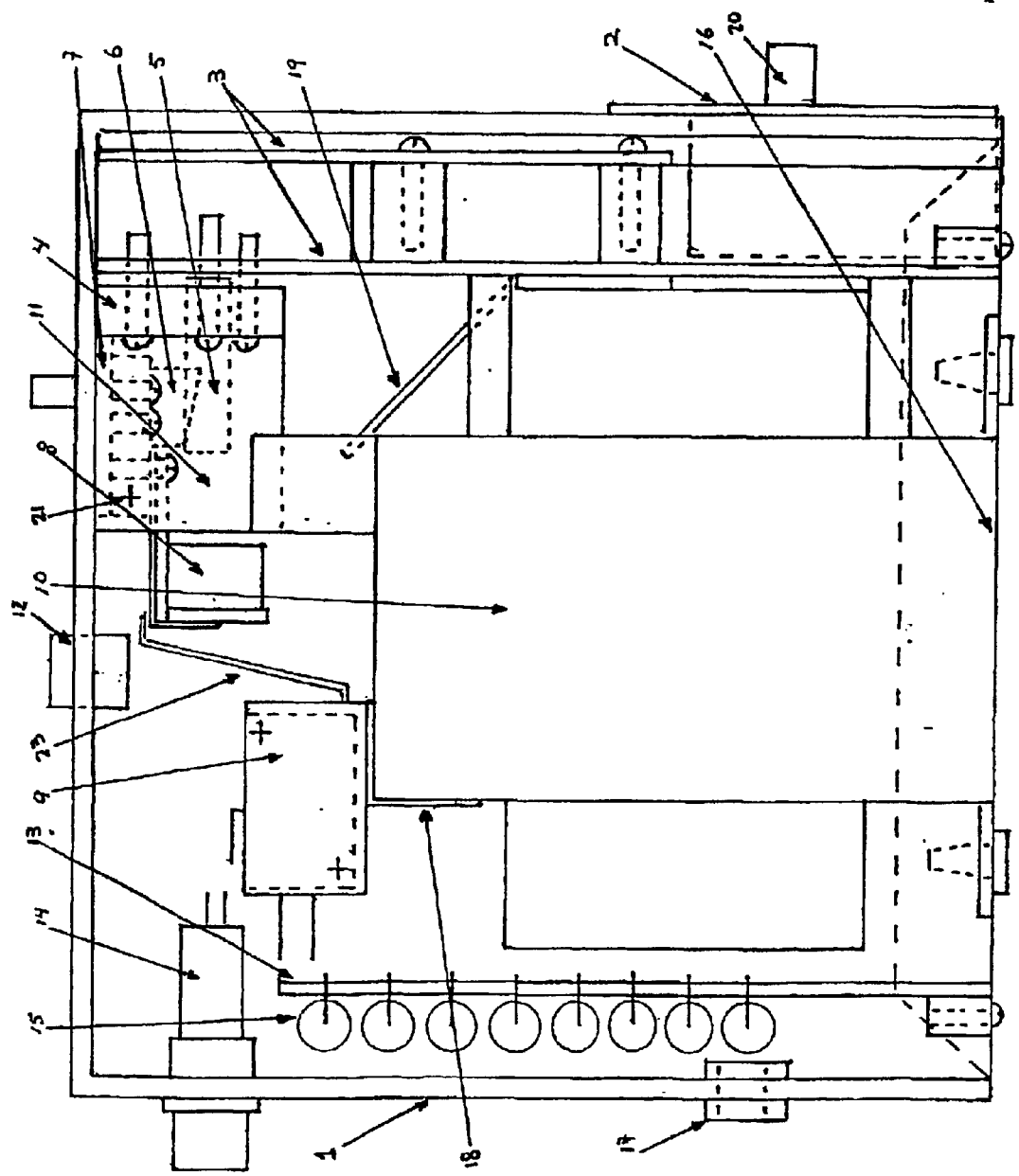
Figura 2

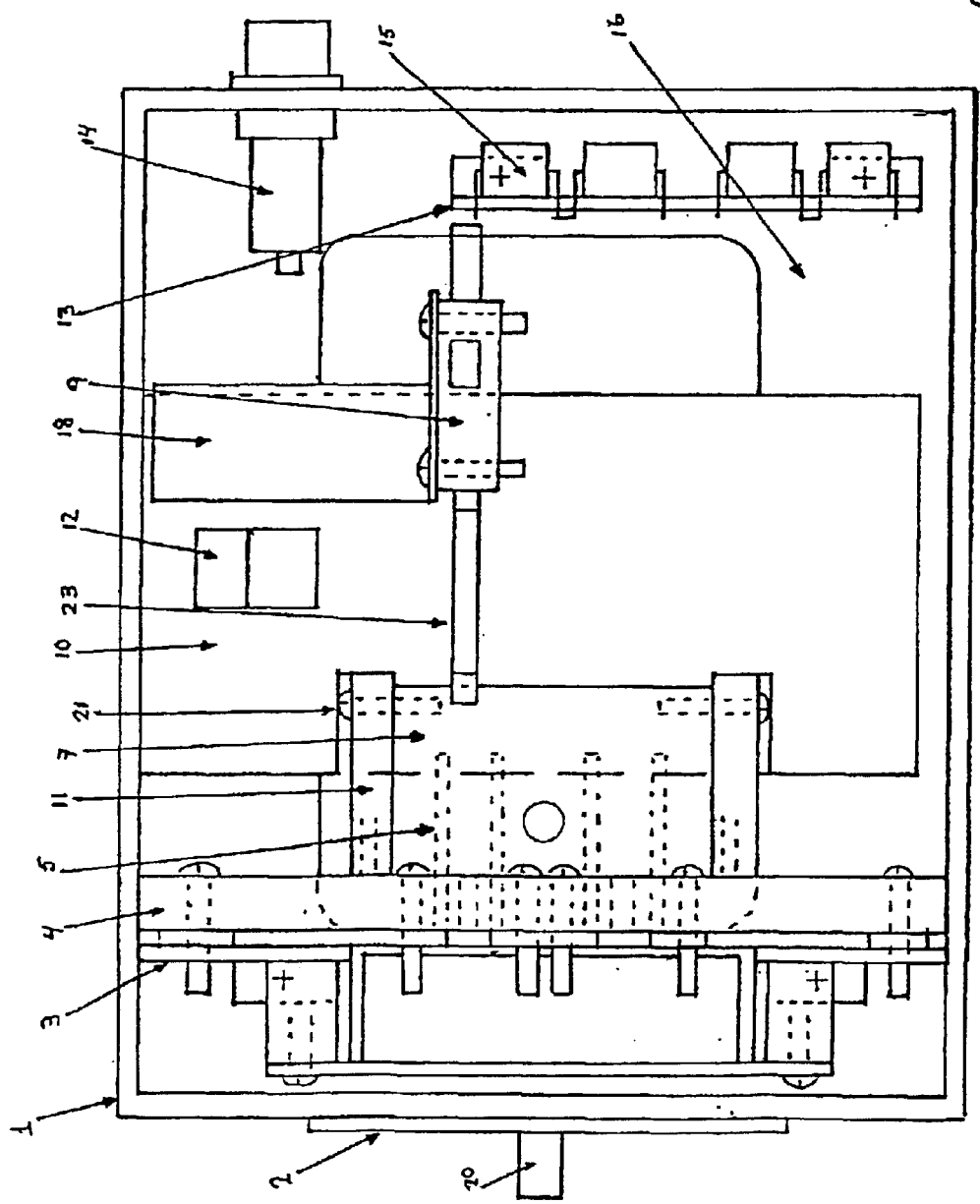
Figura 3

SURGICAL SCALPEL ELECTRICAL INCINERATING DEVICE

FIELD OF APPLICATION

The present invention finds use in all medical establishments, such as hospitals, clinics, consulting offices, etc., that use surgical scalpels and are currently required to destroy them after one use.

BACKGROUND OF THE INVENTION

The Mexican Ministry of Environment, Natural Resources and Fisheries (SEMARNAP) issued an Official Mexican Standard (NOM-087-ECOL-1995), establishing requisites for the treatment of biological or infectious material, including surgical scalpels. At present, major medical facilities have high-capacity incinerators that are used to destroy only organic biological or infectious material, whereas items such as scalpels are, in the best of cases, disposed of with conventional garbage. The standard indicates that surgical scalpels must be treated by mechanical, physical or chemical means (physical means include combustion or incineration), so that they are completely destroyed and unrecognizable and all scrap resulting from their destruction is rendered completely sterile. To prevent reuse of surgical scalpels and subsequent transmission of infections, currently exceedingly large and heavy incinerators are currently used in England, France, Germany, and the United States. These, however, bear no resemblance whatsoever to this particular invention. In fact, the only precedent for this small, portable surgical scalpel incinerator that currently exists is in Mexico, also invented by myself (File No. 9800751, Jan. 27, 1998). However, this new device is completely new and different in both size and design.

Incineration of surgical scalpels is obligatory for all medical establishments in Mexico. Large hospitals and clinics and major medical centers, have the financial means to purchase high-capacity incinerators capable of processing all kinds of infectious or biological waste in large volumes, which are costly to acquire, operate and maintain, while smaller medical establishments such as clinics, laboratories, consulting offices, etc. are unable to purchase such units, The use of large incinerators to destroy scalpels requires that procedures be established to collect, store, handle and transport them, with the risk, in the intervening time, of puncture or cut wounds, as well as the hazard of contagion, independently of the costs the necessary administrative organization entails. In order to reduce these risks, and to enable institutions to incinerate all surgical scalpels immediately after their first use, I undertook to invent a device specifically for incineration of surgical scalpels, using an electromechanism as its main internal component to achieve incineration, in combination with a transformer, an electronic circuit, and electrical elements that satisfy the requisites established by the aforementioned regulation, in addition to offering the benefits of reliable incineration, sterilization of scrap, ease of handling, simple operation, low operating and maintenance costs, reasonable price, small size, and portability.

My invention meets all the requisites and offers all the additional benefits, mentioned above, as surgical scalpels can be incinerated immediately and the unit can be set up for use in all types of medical facilities, including operating theaters.

BRIEF DESCRIPTION OF THE DRAWINGS

FIG. 1 is perspective view of the surgical scalpel incinerator, and shows the internal and external layout of all elements and their components.

FIG. 2 is a side view of the unit, and shows the internal and external layout of all elements and their components.

FIG. 3 is an overhead view of the unit, and shows the internal and external layout of all elements and their components.

DETAILED DESCRIPTION OF THE INVENTION

Figure 4A:
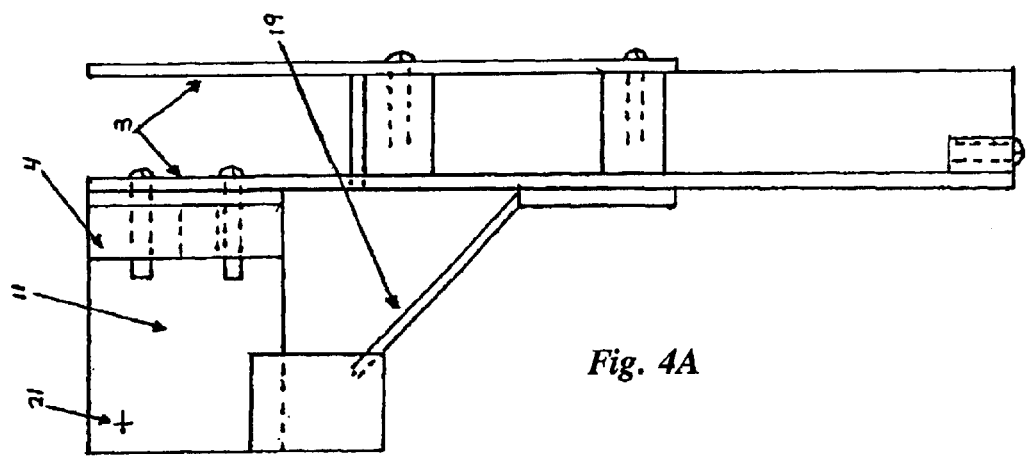
FIG. 4A is a front view of the electromechanism support, its components and their mounting.

FIG. 1 is a perspective view of the surgical scalpel incinerator, showing a cross section of the container 1, with a box at the front 2 in which scalpel scrap is deposited, and which is used to remove said scrap when it is full. The scrap is formed by the electromechanism that makes electrical contact with the scalpel in order to incinerate it. The electromechanism consists of a support 3 (FIGS. 1, 4A, and 4B) and its component elements, including a ceramic plate 4 (FIGS. 1, 3, 4A, 4B, 5B, 5C, 5D, 5E, 5F, and 5G) on which four fixed metal contact plates 5 are mounted (FIGS. 1, 3, 5D, and 5G), which in turn make electrical contact with the scalpel; the ceramic plate is mounted on four struts 11 FIGS. 1, 3, 5B, 5C, 5E, and 5G), which in turn support a rotating door 7 (FIGS. 1, 2, 5A, 5B,and 5C) that turns on a pivot 21 (FIGS. 1, 3, 5A, 5B, 5C, 5E, and 5E). When the door 7 opens, a scalpel can be placed inside the unit; once inside, the scalpel is laid horizontally on a bed formed by the four fixed metal contact plates 5 and five supports 8 mounted on the rotating door 7 (FIGS. 1, 2, 5A, 5B, and 5C). These supports 8 recede as the door 7 closes, leaving the scalpel supported only by the four fixed metal contact plates 5. To ensure that the contact plates 5 make effective electrical contact with the scalpel, when the door 7 is fully closed the three metal pressure plates 6 mounted on the rotating door 7 push the scalpel against the four fixed metal contact plates 5 (see FIGS. 1, 2, 5A, 5B, 5C, and 6A). Opening and closing the rotating door 7 activates several functions: when the door 7 closes, in addition to pushing the scalpel as mentioned above, it also activates the microswitch 9 (FIGS. 1, 2, and 3) by moving its lever 23 (FIGS. 2 and 3), so that it closes the power supply circuit to the transformer 10 (FIGS. 1, 2, and 3), which in turn supplies DC power to the four fixed metal contact plates 5, or so that they receive power from an electronic circuit 15 (FIG. 6B), which in turn is powered by the transformer 10. The components in the electronic circuit are AC rectifying diodes mounted on a circuit card 13 (FIGS. 1, 2, and 3). When the rotating door 7 opens, even when the unit's power switch 12 (FIGS. 1, 2, and 3) indicates (by lighting up) that the equipment is receiving power and is ready for operation, the microswitch 9 is inoperative, as it is open and no power is being supplied to the transformer 10, so that the user can place the scalpel inside the unit without receiving an electric shock. With the door 7 open; the user can also insert a metal object to remove any pieces of scalpel that may have stuck to the fixed metal contact plates 5 during the incineration process.

FIGS. 2 and 3 are side and overhead views of the unit, showing the internal and external layout of the elements in the cabinet 1. Inside the unit, we can see the electromechanism support 7, the electromechanism, consisting of a ceramic plate 4, fixed metal contact plates 5, support struts 11 for the rotating door 7, the pivot 21 for the rotating door 7, the rotating door 7, metal pressure plates 6 mounted on the rotating door 7, the support bed 8 fastened to the rotating door, a chute 19 to guide scrap into the scrap drawer 2, the microswitch 9, the operation of which is described in FIG. 1, the microswitch lever 23 operated by the opening and closing of the door 7, the microswitch support 18, the transformer 10, which supplies electrical current to the fixed metal contact plates 5, or through the electronic circuit formed by rectifying diodes 15 mounted on an electronic circuit card 13. The following components are mounted on the outside of the cabinet 1: fuse holder 14 for the fuse that protects the transformer or electronic circuit, the unit's power switch 12, with an internal light that indicates when the equipment is ready to operate, an outlet for the power cable 17, a chassis 16 that supports the electromechanism, the electronic card 13, the transformer 10, the cabinet 1 and the scrap receptacle 2.

Figure 4B:
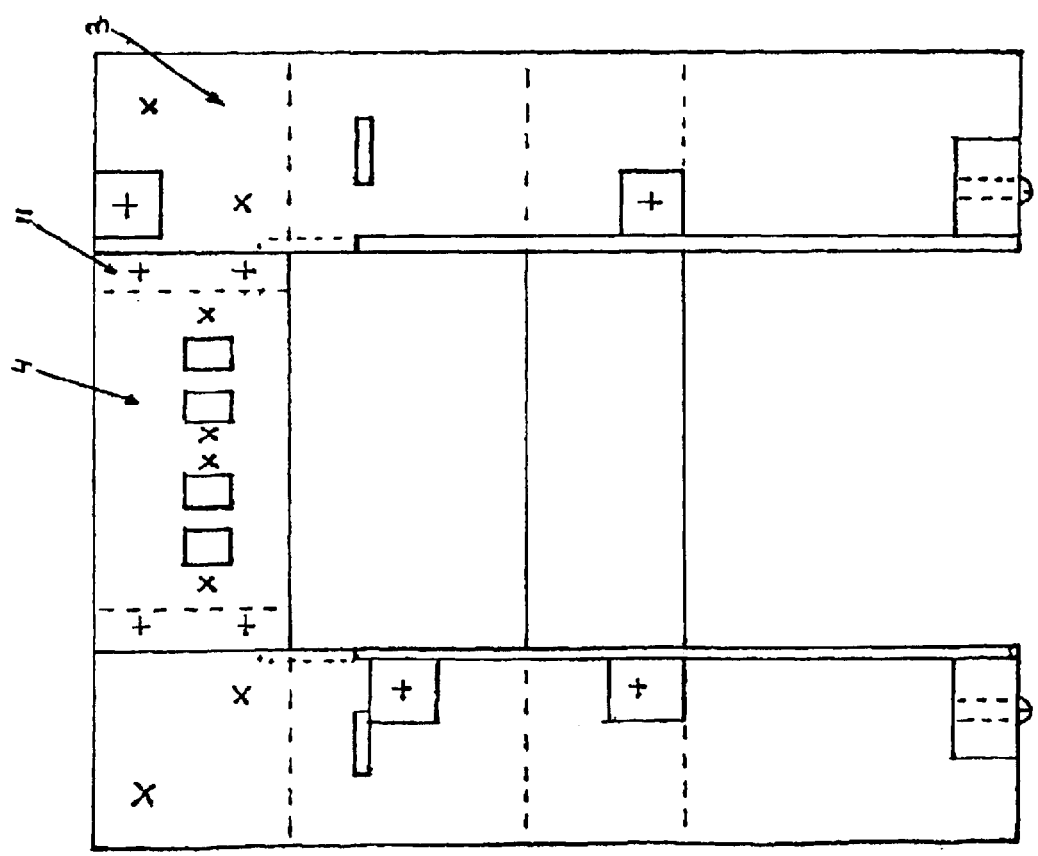
FIG. 4B is a side view thereof.
Figure 5A:
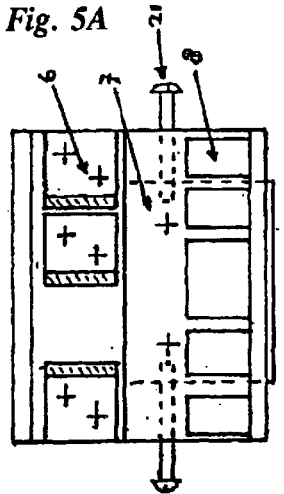
FIG. 5A is a front view of the electromechanism, its components, and their mounting.
Figure 5B:
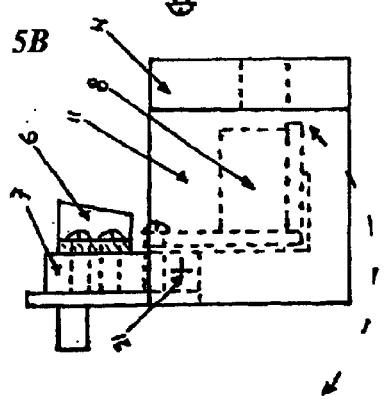
FIGS. 5B and 5C are side views thereof.
Figure 5C:
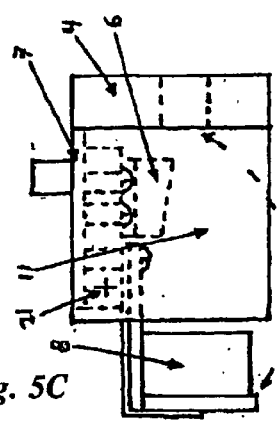
Figure 5F:
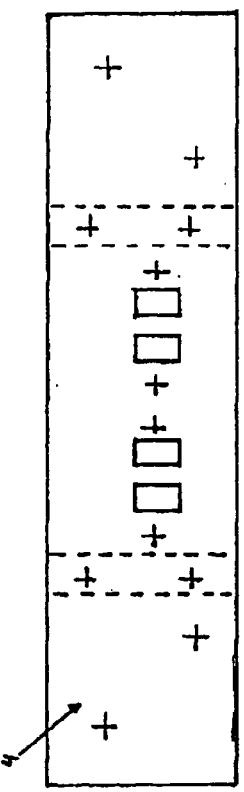
FIG. 5F is a rear view of a portion thereof.
Figure 5D:
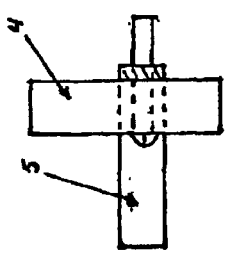
FIGS. 5D and 5E are side views of portions thereof.
Figure 5G:
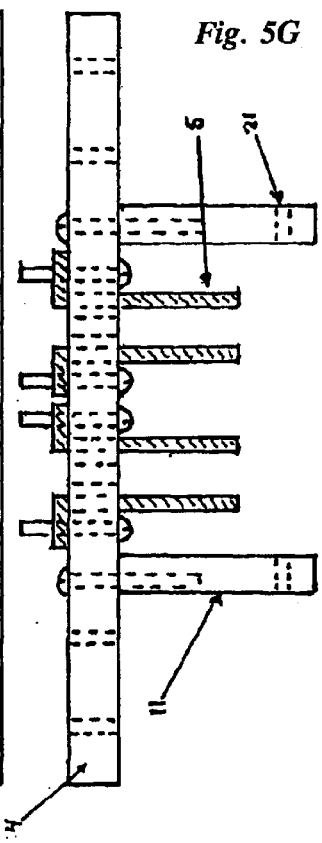
FIG. 5G is a top view of a portion thereof.
Figure 5E:
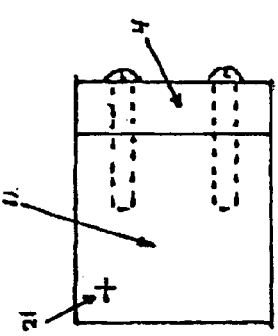

FIGS. 4A and 4B are front and side views of the electromechanism support 3, the ceramic plate 4, the struts 11 of the rotating door 7, the pivot 21 the door turns on, and a ramp or chute 19 to guide scrap into the receptacle 2.

FIGS. 5A–5G are front, overhead and side views of the electromechanism, consisting of: a ceramic plate 4, fixed metal contact plates 5, mounted on the ceramic plate 4, the support struts 11 of the door 7, mounted on the ceramic plate 4, the pivot 21 on which the door 7 turns, metal pressure plates 6, and the support bed 8, mounted on the rotating door 7.

Figures 6A, 6B, 6C:
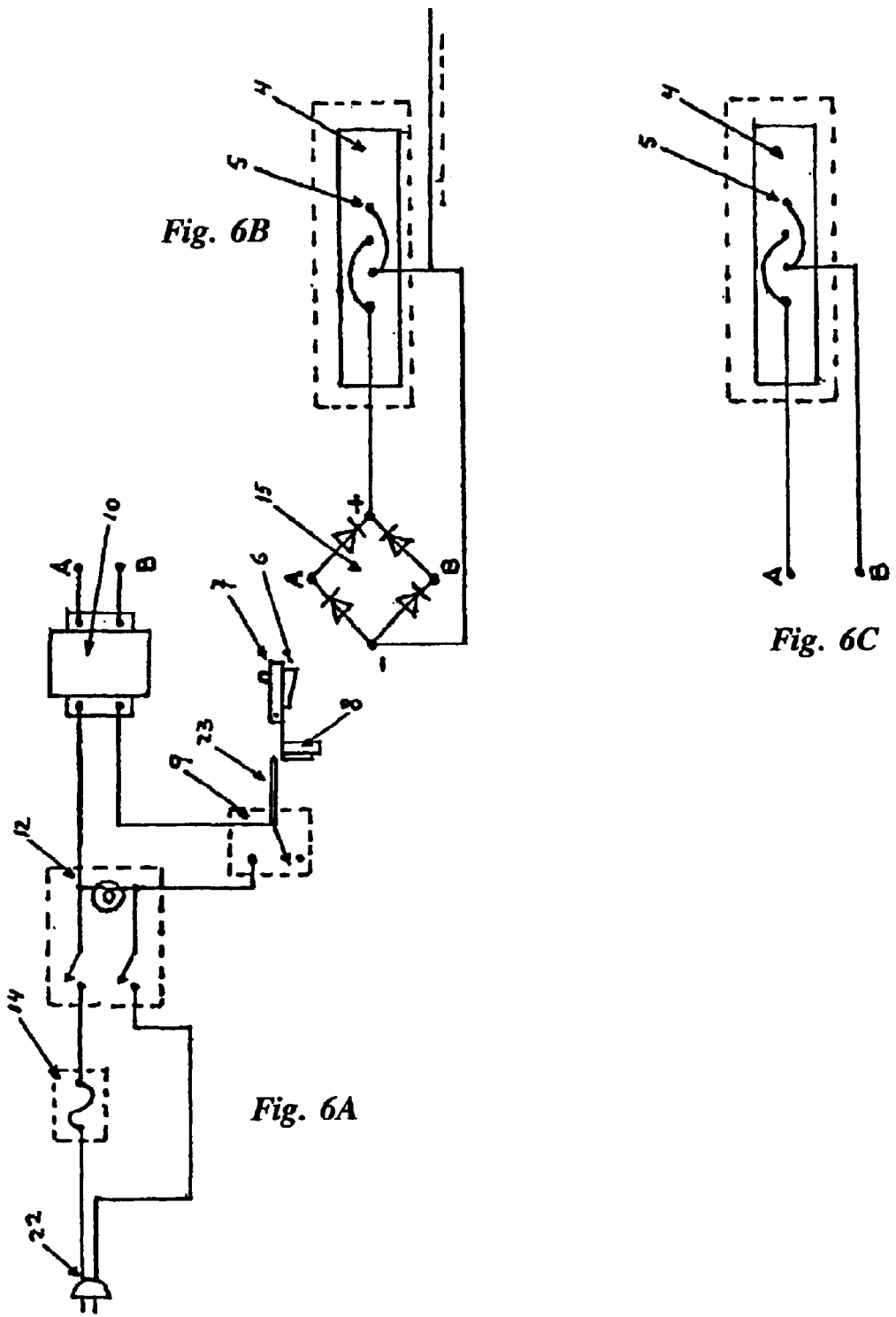
FIGS. 6A, 6B, and 6C are wiring diagrams of the electrical connections between the surgical scalpel incinerator's different components.

FIGS. 6A–6C are wiring diagrams of the device, with connections for all the different elements, including: power supply cable 22, fuse holder 14, power switch 12, microswitch 9, microswitch lever 23, transformer 10, rotating door 7, metal pressure plates 6, and support bed 8. Points A and B show the two options for connecting the transformer 10, either directly to the fixed metal contact plates 4 or to the electronic circuit 15 and from there to the fixed metal contact plates 5 mounted on the ceramic plate 4.

Operating values for the different components are:
Power switch 12: 117 VAC, at 50 amps (with internal light).
Fuse holder 14 (American type) with 15, 30 or 45 amp internal fuse.
Transformer 10: 117–250 VAC, with output of 40, 50, 75, or 100 amps.
Lever-activated microswitch 9: 117–250 VAC, 50 amps.
AC-DC rectifying diodes 15 at 6, 12; 25, 50 or 75 amps.

The cabinet 1 is in two parts: the upper housing (referred to herein as the cabinet 1), and the chassis 16, with the following components mounted on the chassis 16: electronic circuit card support 13, electromechanism support 3, and transformer 10. The following components are mounted on the upper housing (on the cabinet 1): fuse holder 14, power switch 12, and power cable with external plug (not shown in figures), all arranged as shown in FIGS. 1, 2 and 3. The assembly of the chassis 16 with the upper housing, and their respective elements and components, constitutes the surgical scalpel incinerator. The upper housing (the cabinet 1 )and chassis may be made from metal, plastic, or a combination of the two.

Operation

The surgical scalpel incinerator uses an electromechnism, which, as shown in the diagrams, is a combination of mechanical elements whose function is to make contact with the scalpel in order to pass a specified electrical current through it, creating a short circuit that raises the temperature of the scalpel to over 1000 degrees centigrade in under 4 seconds, producing scrap resulting from the deformation or breakage of the scalpel, which in turn is rendered completely sterile. In order for the electromechanism to perform this function, it is supplied with electricity from the electronic circuit, which in turn is powered by the transformer, or connected directly to the transformer 10. The receptacle 2, chassis 16, electrical components, etc. are complementary elements that give the unit its form and enable it to operate.

Manufacture

I have proposed using mass production procedures to manufacture the surgical scalpel incinerator, defining which elements will be manufactured and which will be obtained from third parties for subsequent mounting and assembly, leading in turn to the elaboration of:

Documents for the following procedures: manufacture, assembly and mounting of elements, in addition to safety, training, environmental protection, etc.

Quality control catalogues for: components, raw materials, materials supplied by providers, packing materials, advertising, etc.

Logs for production, quality control, equipment and tool maintenance, cleaning, etc.

Design of production lines, assembly lines, time and movement, etc.

The incinerator has four main elements, as follows:
Electromechanism.
Electronic circuit mounted on support card.
Transformer 10.
Cabinet 1, including chassis 16.
Chassis 16: made with the necessary bends and perforations to mount other elements as shown in the diagrams.
Cabinet: manufactured in three parts with the necessary bends and perforations to chassis, and other elements, to ensure that all perforations are the same size and are made in the same place. Bends in the cabinet will be made by heating if it is plastic, and by mechanical benders if it is metal.
Support and electromechanism: all parts for these elements will be made using templates with the necessary perforations, after which all parts will be assembled.
Transformer and components, including: diodes, switches, power cable with plug, fuse holder, fuse, internal wiring, hardware, etc. will be acquired from third parties under predefined specifications.
Electronic circuit card: will be manufactured with the necessary perforations to mount electronic components.
Manufacture and assembly of the device's elements and components includes the following steps:
   a.—Manufacture of electromechanism components.
   b.—Electromechanism assembly.
   c.—Manufacture of the electronic circuit card and mounting of components.
   d.—Manufacture of chassis and cabinet, and mounting of elements in both.
   e.—Mechanical and electrical connections between components.
   f.—Connection and operating tests.
   g.—Chassis-cabinet connection, sealing of the unit, and second round of operating tests.

Applications

A variety of scalpels are used in medical practice, which standard NOM-087-ECOL-1995 defines as infectious biological waste. This device has been invented to incinerate all types of scalpels, of any length or shape, provided they can be removed from their holder, rendering the resulting scrap completely sterile. We anticipate that the most frequent use of this device will be in hospital operating theaters.

Practical Uses

The surgical scalpel incinerator is intended to assist and facilitate mandatory sanitary practices indicated in the referenced standard with regard to incineration and sterilization of waste. Due to its small size and simple operation, the device can be operated by any person (not necessarily technicians or medical specialists); these benefits, added to its low cost and portability, make it an excellent option for both large and small medical facilities, even those in remote locations, provided they have electricity. This invention will make a great contribution to improving public health care.

What is claim is:

1. Surgical scalpel electrical incinerating apparatus, comprising:
   a cabinet;
   a chassis fastened to said cabinet;
   a support disposed within said cabinet, said support being vertically oriented in said cabinet, said support having a bottom end fastened to said chassis, said support also having a top end;
   a ceramic plate supported by said top end of said support;
   a plurality of fixed metal plates protruding horizontally from said ceramic plate, said plurality of metal plates being fastened to said ceramic plate, said plurality of metal plates being electrically connected to an electrical power source;
   said plurality of fixed metal plates being configured to receive a surgical scalpel blade which is to be incinerated;
   first and second struts attached to said ceramic plate, said first and second struts projecting horizontally proximate said plurality of metal plates;
   first and second pivots projecting from each of said first and second struts, respectively, toward the other of said first and second struts;
   a door rotatably supported by said first and second pivots and proximate said plurality of metal plates, said door having a bottom face, said door being rotatable from a vertical orientation wherein said bottom face faces horizontally, to a horizontal orientation wherein said bottom face is placed above and in proximity with said plurality of metal plates;
   a support structure fixed to said door and rotatable therewith such that, when said door is in said vertical orientation, said support structure projects upward between said plurality of metal plates, and when said door is in said horizontal orientation, said support structure is withdrawn from between said plurality of metal plates;
   a plurality of pressure plates fixed to said bottom face of said door and projecting therefrom, such that, when said door is in said horizontal orientation, said pressure plates project toward said plurality of metal plates so as to urge any object that rests upon said plurality of metal plates into contact with said plurality of metal plates;
   said plurality of metal plates supplying electrical current from said electrical power source through portions of an electrically conductive object resting upon said plurality of metal plates when said door is in said horizontal orientation,
   whereby said electrically conductive object is electrically heated.

2. Apparatus as set forth in claim 1, comprising a power switch, a power cable entry, and a fuse holder mounted on an outer surface of said cabinet.

3. Apparatus as set forth in claim 1, comprising an electrical switch operatively connected to said power supply and to said door, such that when said door is in said vertical orientation, said power supply is electrically disconnected from said plurality of metal plates.

4. Apparatus as set forth in claim 1, comprising a transformer, a support card, an electronic circuit for rectifying alternating current, and a power supply cable.

5. Apparatus as set forth in claim 1, comprising a scrap recepticle and a hopper located beneath said plurality of metal plates for guiding scrap of the incinerated scalpels into said scrap receptacle.

6. A surgical scalpel electrical incinerating device, comprising:
   a cabinet;
   a plurality of electrical contacts supported and enclosed therein and so connected to an electrical power source as to provide at least one pair of said contacts whose members are electrically connectable to opposite poles of said electrical power source;
   a door in said cabinet, said door being placed proximate said plurality of electrical contacts and being openable to provide access to said plurality of electrical contacts and closable to block access thereto;
   a switch operatively coupled to said door and to said electrical power supply and to said plurality of electrical contacts, such that said plurality of contacts are capable of forming a closed electrical circuit with said power supply only when said door is closed.

7. A device as set forth in claim 6, wherein said plurality of electrical contacts are distributed horizontally to form a receiving surface,
   said device comprising at least one supporting structure movably disposed proximate said plurality of electrical contacts,
   said supporting structure being electrically isolated from said plurality of contacts and from said electric power supply,
   said supporting structure being so coupled to said door as to form a supporting surface above said receiving surface when said door is open and not when said door is closed.

8. A device as set forth in claim 6, comprising a pressure-exerting structure, operatively coupled to said door, so positioned relative to said plurality of conductors as to define a pressure-exerting surface which is approximated to said plurality of electrical contacts when said door is closed.

9. A device as set forth in claim 6, comprising a drawer located on said cabinet, a hopper so positioned in said door and so positioned with reference to said plurality of electrical contacts as to receive debris falling from said plurality of electrical contacts.

10. A method of incinerating a surgical scalpel blade, comprising the steps of:
    placing the blade proximate a plurality of electrically conductive bodies;
    enclosing the blade and said plurality of bodies;
    causing the blade to contact said plurality of bodies; and
    supplying electric current through the blade, via said plurality of bodies, only while the blade and plurality of bodies are enclosed.

11. A method as set forth in claim 10, comprising the step of mechanically urging the blade against said plurality of bodies while enclosing the blade and said plurality bodies.

12. A method as set forth in claim 10, comprising the step of collecting debris of the blade in a receptacle located beneath said plurality of bodies after the blade is incinerated.

13. A method as set forth in claim 10, comprising the step of supporting the blade proximate said plurality of bodies and not in contact therewith, after said step of placing the blade proximate said bodies and before said step of causing the blade to contact said plurality of bodies.

* * * * *